United States Patent [19]

Shimada et al.

[11] 4,438,093
[45] Mar. 20, 1984

[54] ORAL COMPOSITION CONTAINING DEXTRANASE AND α-1,3 GLUCANASE AND A METHOD FOR PREVENTING AND SUPPRESSING ORAL DISEASES USING THE SAME

[75] Inventors: Kazuo Shimada, Nakatado; Masataka Akiyama, Kanonji; Masami Sudo, Mitoyo, all of Japan

[73] Assignee: The Research Foundation for Microbial Diseases of Osaka University, Osaka, Japan

[21] Appl. No.: 364,182

[22] Filed: Mar. 31, 1982

[30] Foreign Application Priority Data

Apr. 3, 1981 [JP] Japan .................. 56-51004

[51] Int. Cl.³ .................. A61K 7/28; A61K 37/48
[52] U.S. Cl. .................. 424/50; 424/94
[58] Field of Search .................. 424/50, 93

[56] References Cited

U.S. PATENT DOCUMENTS

| 3,622,661 | 11/1971 | King | 424/50 |
| 3,912,594 | 10/1975 | Shimada et al. | 195/65 |
| 4,115,546 | 9/1978 | Vidra et al. | 424/50 |
| 4,335,101 | 6/1982 | Stoudt et al. | 424/50 |
| 4,340,673 | 7/1982 | Stoudt et al. | 435/97 |
| 4,353,891 | 10/1982 | Guggenheim et al. | 424/50 |

FOREIGN PATENT DOCUMENTS

| 50-58243 | 5/1975 | Japan . |
| 51-67346 | 6/1976 | Japan . |
| 53-35136 | 9/1978 | Japan . |
| 55-15443 | 4/1980 | Japan . |
| 55-69504 | 5/1980 | Japan . |
| 55-50006 | 12/1980 | Japan . |
| 55-167215 | 12/1980 | Japan . |
| 1373487 | 11/1974 | United Kingdom . |
| 1385095 | 2/1975 | United Kingdom . |

OTHER PUBLICATIONS

R D-181-07S Anonymous (5/10/79) Mutanase and Glucose Oxidase.
SW-7711-735 Schweizer Fermont (5/6/79) Mutanase and Doxtranase pp. Oral Hygeine Composation.
Guggenheim et al. Chem. Abstr. 77 #110009g (1972) of Caries, Res. 1972 6(4); 289-297.
Frank et al. Chem. Abstr. 80 #116667d (1974) of J. Biol. Ruccale 1973 1(3): 273-280.
Klein et al. Chem. Abstr. 81 #74399f (1974) of J. Biol. Buccale 1973 1(4): 293-300.
Regulati et al. Chem. Abstr. 82 #68380x (1975) of Helv. Odontol. Acta (1974) 18(2): 97-100.
Litzler et al. Chem. Abstr. 82 #106518h (1975) of J. Biol. Buccale (1974) 2(4): 395-400.
Guggenheim et al. Chem. Abstr. 92 #104475f (1980) of Caries Res. 1980 14(3): 130-7.
Takahashi et al. Chem. Abstr. 93 #128480u (1980) of Bull Tokyo Meddentuniv 1980 27(2) 79-88.
Sunstar Chem. Abstr. 94 #109104d (1981) of JPN. Kokai T. L. 80, 167, 215 Dec. 26, 1980.
Takahashi et al. Chem. Abstr. 93 #181808h (1980) of Kokubyo Gakkai Zassh 1 (1980) 47(2): 240-6.

*Primary Examiner*—Shep K. Rose
*Attorney, Agent, or Firm*—Armstrong, Nikaido, Marmelstein & Kubovcik

[57] ABSTRACT

An oral composition which comprises a pharmaceutically acceptable carrier, dextranase and α-1,3 glucanase, said dextranase being present in an enzyme unit ratio of 1:2 to 2:1 relative to said α-1,3 glucanase. The oral composition according to the present invention exhibits a synergistic effect of dextranase and α-1,3 glucanase and is highly effective for not only preventing but also suppressing various oral diseases such as dental caries, gingivitis and alveolar pyorrhea.

7 Claims, 1 Drawing Figure

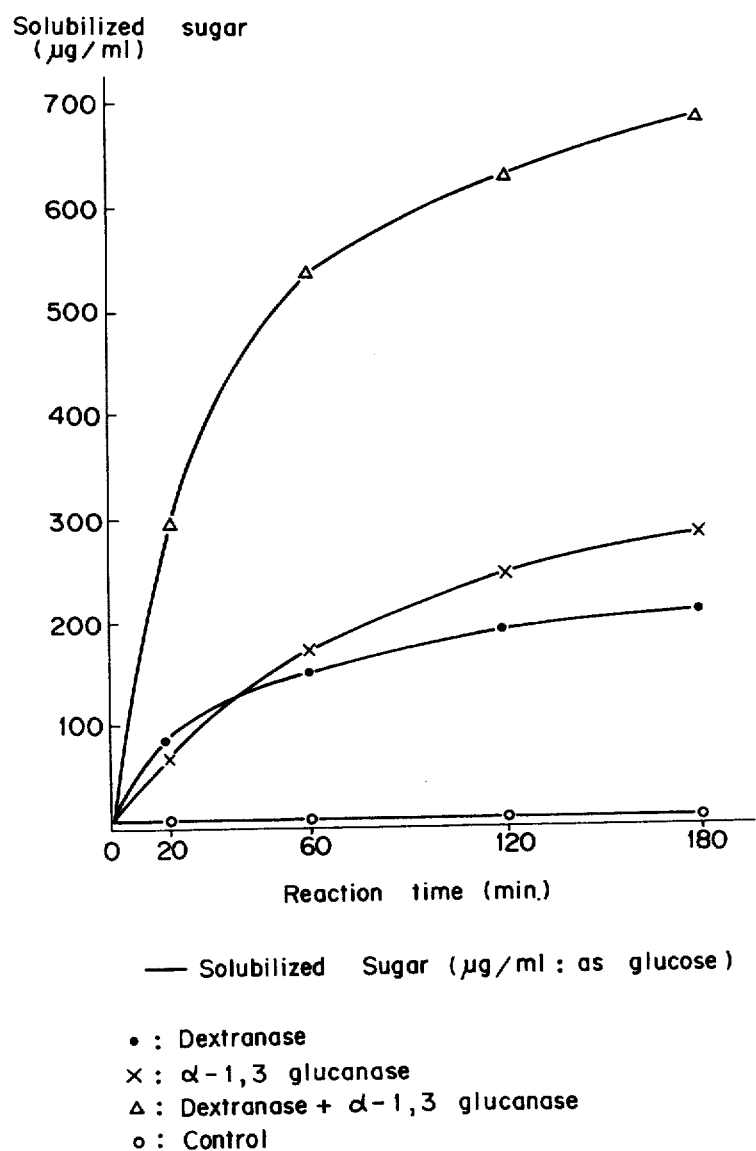

ORAL COMPOSITION CONTAINING DEXTRANASE AND α-1,3 GLUCANASE AND A METHOD FOR PREVENTING AND SUPPRESSING ORAL DISEASES USING THE SAME

The present invention relates to an oral composition. More particularly, this invention is concerned with an oral composition which comprises a pharmaceutically acceptable carrier, dextranase and α-1,3 glucanase and which is highly effective not only in prevention of various oral diseases such as dental caries, gingivitis and alveolas pyorrhea but also in suppression of such various oral diseases.

It is well known to those skilled in the art that dental caries and gingivitis are induced by the formation of dental plaque. The dental plaque is formed through adhesion of viscous glucans to the teeth and gingivae. Such glucans are produced from sucrose by the action of caries-causing streptococci always found in the oral cavity. Therefore, degradation and removal of the glucans adhering to the teeth and gingivae may be very effective for preventing oral diseases such as dental caries. In view of this, there have been proposed various techniques for dissolving and removing the glucans, for example, by hydrolysis with dextranase or α-1,3 glucanase (see, for example, Japanese Patent Application Laid-Open Publication No. 58243/1975, Japanese Patent Publication No. 35136/1978, Japanese Patent Publication No. 15443/1980, Japanese Patent Publication No. 50006/1980, U.S. Pat. Nos. 3,622,661, 3,912,594 and 4,115,546). However, satisfactory preventing effect against dental caries cannot be expected in such prior art. The reason therefor appears to be as follows. The glucans responsible for dental plaque may, in general, be divided roughly into two groups, i.e., a water-soluble dextran (hereinafter frequently referred to as "dextran") and a water-insoluble glucan (hereinafter often referred to as "insoluble glucan"). The dextran has a large proportion of α-1,6 glucosidic linkage and can be completely hydrolyzed only with dextranase which can specifically cleave the α-1,6 glucosidic linkage. By contrast, the insoluble glucan has a large proportion of α-1,3 glucosidic linkage and can be completely hydrolyzed only with α-1,3 glucanase which can specifically cleave the α-1,3 glucosidic linkage. In other words, because of the specific relationship between an enzyme and a substrate, dextranase alone cannot completely hydrolyze insoluble glucan into lower molecular sugar while α-1,3 glucanase along cannot completely hydrolyze dextran into lower molecular sugar. Accordingly, it is difficult to sufficiently prevent dental plaque formation and dissolve and remove the dental plaque by the use of only one of both the enzymes as can be seen in the above prior art.

For this reason, a combined use of dextranase and α-1,3 glucanase has been proposed to degrade and remove simultaneously both dextran and α-1,3 glucan responsible for the formation of dental plaque. As an example of the combined use of dextranase and α-1,3 glucanase, reference may be made to B. Guggenheim et al., "Caries and Plaque Inhibition by Mutanase in Rats", Caries Res., 6, 289-297(1972). In the Caries Res., Guggenheim et al. disclose that the extent of plaque in the rats harbouring their normal flora is not significantly affected by both the enzymes, i.e., dextranase and α-1,3 glucanase (mutanase), even by the simultaneous administration of both the enzymes. Guggenheim et al. also disclose that in the rats kept in relative gnotobiosis, both dextranase and α-1,3 glucanase are effective in reducing plaque and the simultaneous administration of both the enzymes results in an additive effect. However, it is difficult to say that a sufficient effect of the simultaneous administration of α-1,3 glucanase and dextranase on the prevention of dental caries of the rats kept in relative gnotobiosis is attained because the data obtained make no sense in view of the standard error. Further, Guggenheim et al. fail to disclose any effect of the simultaneous use of dextranase and α-1,3 glucanase on the prevention of dental caries of field animals.

Meanwhile, British Pat. No. 1385095 discloses an oral preparation comprising dextranase and cariogenanase. However, the cariogenanase used in the oral preparation is different from α-1,3 glucanase in kind of enzyme. Illustratively stated, the substrate of cariogenanase is cariogenan which is an unbranched glucan possessing α-(1→3) and α-(1→2) links in a ratio of about 3:1. That is, cariogenanase cleaves specifically an α-(1→3) glucosidic linkage while a vicinal α-(1→2) linkage remains intact. Further, cariogenanase is inactive on nigeran and nigerose. By contrast, it is well known to those skilled in the art that α-1,3 glucanase cleaves specifically α-1,3 glucan which is a branched glucan possessing a large proportion of α-(1→3) and a small proportion of α-(1→6) or α-(1→4) links and that nigeran and nigerose are substrates for α-1,3 glucanase.

As is apparent from the foregoing, an oral composition comprising as the active ingredients both dextranase and α-1,3 glucanase has not been developed which is remarkably effective for preventing oral diseases as compared with an oral composition comprising as the active ingredient dextranase alone or α-1,3 glucanase alone.

In view of the above, the present inventors have made extensive and intensive researches on an effective combined use of dextranase and α-1,3 glucanase with a view to developing an oral composition which is very useful for preventing oral diseases.

As a result, the present inventors have unexpectedly found that oral diseases can be not only prevented but also suppressed by the combined administration of dextranase and α-1,3 glucanase in an enzyme unit ratio of 1:2 to 2:1. Further, the present inventors have unexpectedly and surprisingly found that the combined use of dextranase and α-1,3 glucanase in the above-mentioned ratio has a synergistic effect on both prevention and suppression of oral diseases. The present invention has been completed based on such novel findings. The term "enzyme unit" for dextranase use herein is a criterion of the activity of dextranase, and "one enzyme unit" for dextranase is defined as the enzyme amount capable of liberating 1 $\mu$M reducing sugar as glucose per minute from dextran. The method for measuring the activity of dextranase will be described later. The term "enzyme unit" for α-1,3 glucanase used herein is a criterion of the activity of α-1,3 glucanase, and "one enzyme unit" for α-1,3 glucanase is defined as the enzyme amount capable of liberating 1 $\mu$M reducing sugar as glucose per minute from insoluble glucan. The method for measuring the activity of α-1,3 glucanase will be described later.

Accordingly, it is an object of the present invention to provide an oral composition comprising as the active ingredients dextranse and α-1,3 glucanase which prevents oral diseases very effectively.

The foregoing and other objects, features and advantages of the present invention will be apparent to those skilled in the art from the following detailed description and appended claims taken in connection with the accompanying drawing in which:

FIGURE is a graph showing the substrate-degrading activity of dextranase and α-1,3 glucanase with respect to the case where they are used alone and with respect to the case where they are used in combination.

In accordance with one aspect of the present invention, there is provided an oral composition which comprises a pharmaceutically acceptable carrier, dextranase and α-1,3-glucanase, said dextranase being present in an enzyme unit ratio of 1:2 to 2:1 relative to said α-1,3 glucanase.

In accordance with another aspect of the present invention, there is provided a method for preventing and suppressing oral diseases which comprises administering to a patient an effective amount of an oral composition which comprises a pharmaceutically acceptable carrier, dextranase and α-1,3 glucanase, said dextranase being present in an enzyme unit ratio of 1:2 to 2:1 relative to said α-1,3 glucanase.

It is well known to those skilled in the art that each of dextranase and α-1,3 glucanase has the endo-type and the exo-type. According to the present invention, both the endo type and the exo type of each of dextranase and α-1,3 glucanase may be used as the active ingredients of an oral composition. However, when the exo-type of each of dextranase and α-1,3 glucanase is used, they should each be incorporated into a carrier in a large amount to attain a sufficient oral disease preventive effect. Therefore, from the standpoint of the amount to be incorporated into the carrier and the oral disease-inhibiting effect, it is preferred that the endo-type dextranase and the endo-type α-1,3 glucanase be employed as the active ingredients in an oral composition of the present invention.

With respect to microorganisms capable of producing dextranase, there is known microorganisms such as moulds, e.g., fungi belonging to the genus Penicillium, Aspergillus, Spicaria, Chaetomium, Verticillium, Fusarium and Helminthosporium, bacteria, e.g., those belonging to the genus Lactobacillus, Cellvibrio, Cytophaga, Brevibacterium, Pseudomonas, Flavobacterium and Corynebacterium.

The dextranase which may be employed as one of the active ingredients of the present oral composition may be one produced from any of the above-listed moulds and bacteria. However, among the dextranases produced from the above-mentioned microorganisms, the dextranase produced from microorganisms belonging to the genus Corynebacterium is preferably used as one of the active ingredients of the present oral composition because such dextranase exerts a particularly excellent preventive and suppresive effects on oral diseases when it is used in combination with α-1,3 glucanase. As examples of microorganisms which are preferably employed for producing detranase to be employed in the present oral composition, there may be mentioned a strain Corynebacterium AK-01 (deposited with Technical Research Institute of Microbial Industry, Agency of Industrial Science & Technology, Japan, as an accession number FERM No. 2505) and all mutants which may be produced from the microorganisms belonging to the genus Corynbacterium by means of various variation methods such as ultraviolet ray irradiation, X-ray irradiation, nitrosoguanidine treatment, nitrogen mustard treatment and nitrous acid treatment and are capable of producing dextranase, for instance, such mutants showing protease-negative and cellulose-negative, or artificial mutants.

A dextranase to be used as one of the active ingredients of the present oral composition may be produced from the above-mentioned microorganisms by means of conventional dextranase-producing methods as described in, for example, Jan-Christer Janson and Jerker Porath, Methods in Enzymology, 8,615–621 (1966); Chalet et al., Applied Microbiology vol. 20, No. 3,421–426 (1970); Fukumoto et al., J. Biochem., 69,1113–1121 (1971); Hanada et al., Agricaltural and Biological Chemistry, 48, No. 1, 15–26 (1974); Japanese Patent Publication No. 47-37029 (1972); U.S. Pat. No. 3,912,594; and Japanese Patent Publication No. 53-46918 (1978). Among the dextranase-producing methods mentioned above, the method as disclosed in Japanese Patent Publication No. 53-46918 (1978) is preferably employed for producing dextranase to be used as one of the active ingredients of the present oral composition from the standpoint of ease in procedure and of economy because this method does not require an inducer and from the standpoint of activity of the prepared dextranase.

A representative example of the methods for producing dextranase to be used as one of the active ingredients of the present oral composition will be described hereinbelow.

In order to produce dextranase, a dextranase-producing microorganism is cultivated in a natural or synthetic nutrient medium. The nutrient medium to be employed may be either of liquid or solid type, but it is preferable for production on a commercial scale to employ a liquid nutrient submerged culture with aeration-agitation. Nutrient sources of the medium may be any of those usually utilized in the art for cultivation of a microorganism. For example, as assimilable carbon sources, such materials as dextran, saccharose, citrates, soluble starch and mollasses may be employed. As the source of nitrogen in the nutrient medium, such materials as peptone, meat extract, yeast extract, casein hydrolysate, defatted soybean powder, and ammonium salts may be employed. As inorganic salts, such salts as those with phosphoric acid, magnesium or potassium may be employed. A dextran, for example, "Dextran T10" (manufactured and sold by Pharmacia Co., Ltd., Uppsala, Sweden) or a dextran produced by the action of dental caries-causing streptococci may advantageously be, as an inducer, incorporated into the nutrient medium to obtain a high yield of dextranase. The cultivation temperature ranges from 5° to 37° C., preferably from 20° to 37° C. The pH value of culture medium may be adjusted at 5.5 to 9.0, preferably at 6.5 to 8.5. The cultivation period varies depending on other cultivation conditions, but it is usually about 3 to 7 days in stationary culture or about 1 to 2 days in aeration-agitation culture. The cultured broth wherein the microorganism had abundantly grown under the above-mentioned conditions is subjected to sterile centrifugation to separate the crude enzyme solution from the cultured broth. The crude enzyme solution thus prepared may be purified by means of conventional methods such as concentration under reduced pressure, salting out with ammonium sulfate, precipitation with a solvent and column fractionation, which may be employed alone or in combination.

The activity of dextranase thus produced is measured as follows.

"Dextran T70" (trade name of a dextran manufactured and sold by Pharmacia Co., Ltd., Uppsala, Sweden) is employed as substrate. To 4 ml of a 2.5 w/v % solution of the dextran is added 14 ml of a 0.02 M phosphate buffer solution and 2 ml of the enzyme solution. The resulting mixture is allowed to stand at 40° C. for 10 minutes under a pH of 7.0 and then an increased amount of reducing sugar is determined by means of the Somogyi-Nelson method [M. Somogyi, J. Biol. Chem., 195,19 (1952)]. One enzyme unit for dextranase is defined to be the enzyme amount capable of liberating 1 $\mu$M reducing sugar as glucose per minute from dextran.

Meanwhile, with respect to microorganisms capable of producing $\alpha$-1,3 glucanase, there are known microorganisms such as moulds, e.g., fungi belonging to the genus Penicillium and Trichoderma harzianum, bacteria, e.g., those belonging to the genus Pseudomonas and Flavobacterium.

The $\alpha$-1,3 glucanase which may be employed as one of the active ingredients of the present oral composition may be one produced from any of the above-listed moulds and bacteria. However, among the $\alpha$-1,3 glucanases produced from the above-mentioned microorganisms, the $\alpha$-1,3 glucanase produced from microorganisms belonging to the genus Pseudomonas is most preferably used as one of the active ingredients of the present oral composition because such glucanase exerts a particularly excellent preventive and suppressive effects on oral diseases when it is used in combination with dextranase. As examples of microorganisms which are preferably employed for producing $\alpha$-1,3 glucanase to be employed in the present oral composition, there may be mentioned a strain Pseudomonas SK-01 (deposited with Technical Research Institute of Microbial Industry, Agency of Industrial Science & Technology, Japan, as an accession number FERM No. 4273) and all mutants which may be produced from the microorganisms belonging to the genus Pseudomonas by means of various conventional variation methods and are capable of producing $\alpha$-1,3 glucanase, for instance, such mutants showing protease-negative and cellulose-negative, or artificial mutants.

A $\alpha$-1,3 glucanase to be used as one of the active ingredients of the present oral composition may be produced from the above-mentioned microorganisms by means of conventional $\alpha$-1,3 glucanase-producing methods as described in, for example, Shiro Hasegawa and John H. Nordin, J. Biol. Chem., 244(20), 5460–5470 (1969); Kohei Imai et al., Agri. Biol. Chem., 41(8), 1339–1346 (1977); Kohei Imai et al., Agric. Biol. Chem., 41(10), 1889–1895 (1977); Tsunoda et al., Agric. Biol. Chem., 42(5), 1045–1053 (1978); Guggenheim et al., J. Dent. Res., 51,394–402 (1972); Japanese Patent Publication No. 50-20155 (1975); and Japanese Patent Publication No. 56-1070 (1981).

Among $\alpha$-1,3 glucanase-producing methods mentioned above, the method as disclosed in Japanese Patent Publication No. 56-1070 (1981) is preferably employed for producing $\alpha$-1,3 glucanase to be used as one of the active ingredients of the present oral composition from the standpoint of ease in procedure and of economy because this method does not require an inducer and from the standpoint of activity of the prepared $\alpha$-1,3 glucanase.

A representative example of the methods for producing $\alpha$-1,3 glucanase to be used as one of the active ingredients of the present oral composition will be described hereinbelow.

In order to produce $\alpha$-1,3 glucanase, a $\alpha$-1,3 glucanase-producing microorganism is cultivated on a natural or synthetic nutrient medium. The nutrient medium to be employed may be either of liquid or solid type, but it is preferable for production on a commercial scale to employ a liquid nutrient submerged culture with aeration-agitation. Nutrient sources of the medium may be any of those usually utilized in the art for cultivation of a microorganism. For example, as the nutrient sources, there may be mentioned starch, soluble starch, maltose, galactose, dextrose, soybean powder, corn steep liquor, peptone, meat extract, casein, inorganic nitrogen, various inorganic salts and various metallic ions. An $\alpha$-1,3 glucan may advantageously be, as an inducer, incorporated into the nutrient medium to obtain a high yield of $\alpha$-1,3 glucanase. The cultivation temperature ranges from 10° to 37° C., preferably from 20° to 30° C. The pH value of culture medium may be adjusted at 5.0 to 8.0, preferably 6.0 to 7.5. The cultivation period varies depending on other cultivation conditions, but it is usually about 1 to 3 days. The cultured broth wherein the microorganism has abundantly grown under the above-mentioned conditions is subjected to sterile centrifugation to separate the crude enzyme solution from the cultured broth.

The crude enzyme solution thus prepared may be incorporated into a pharmaceutically acceptable carrier together with dextranase as the active ingredients. But it is preferred that the crude enzyme solution is purified by means of conventional methods such as concentration with a membrane; concentration under reduced pressure; salting out with ammonium sulfate, sodium sulfate or the like; differential precipitation with a solvent such as acetone or ethanol; and isoelectric point precipitation. These methods may be carried out alone or in combination.

The activity of $\alpha$-1,3 glucanase thus produced is measured as follows.

An insoluble glucan of a strain Streptococcus mutans OMZ-176 (a dental caries-causing streptococcus) is used as the substrate. To 8 ml of a 5 w/v % suspension of the insoluble glucan is added 10 ml of 0.02 M phosphate buffer solution, 3 ml of distilled water and 2 ml of the enzyme solution. The resulting mixture is allowed to stand at 40° C. for 5 minutes under a pH of 6.5 and then an increased amount of reducing sugar is determined by means of the Somogyi-Nelson method [M. Somogyi, J. Biol. Chem., 195,19 (1952)]. One enzyme unit for $\alpha$-1,3 glucanase is defined to be the enzyme amount capable of liberating 1 $\mu$M reducing sugar as glucose per minute from an insoluble glucan.

As mentioned above, the present oral composition comprises dextranase and $\alpha$-1,3 glucanase and a pharmaceutically acceptable carrier. As the pharmaceutically acceptable carrier, there may be mentioned a non-consumable carrier such as a tooth paste, a tooth powder, a tooth solid, a mouth rinse, a mouth spray, a rubing ointment, a chewing gum, an application sponge and a denture treating agent; and a consumable carrier such as a candy drop, food, a beverage, a chocolate, a troche, a caramel, a lozenge and a piece of taffy.

According to the present invention, it is essential that the enzyme unit ratio of dextranase to $\alpha$-1,3 glucanase in the composition be 1:2 to 2:1. When the oral composition containing as the active ingredients dextranase and $\alpha$-1,3 glucanase in the above-mentioned enzyme unit ratio is used for oral hygiene, oral diseases such as dental caries can be very effectively prepared and suppressed by the synergistic effect exerted by the combined use of dextranase and α-1,3 glucanase in a specific enzyme unit ratio. By contrast, when the enzyme unit ratio of dextranase to α-1,3 glucanase is not within the above-mentioned ratio, such a synergistic effect due to the combined use of dextranase and α-1,3 glucanase is not exerted.

According to the present invention, it is preferred that each of dextranase and α-1,3 glucanase be contained in the oral composition in an amount of at least 0.5 enzyme unit per gram of the oral composition from the standpoint of effectiveness. The upper limit of the amount of dextranase and α-1,3 glucanase contained in the oral composition is not critical. But from the standpoint of economy, each of dextranase and α-1,3 glucanase may generally be contained in the oral composition in an amount of not more than 100 enzyme units per gram of the oral composition. Therefore, in the present invention it is preferred that an oral composition contain each of dextranase and α-1,3 glucanase in an amount of 0.5 to 100 enzyme units per gram of the oral composition, more preferably 0.5 to 10 enzyme units per gram of the oral composition.

As mentioned above, according to another aspect of the present invention, there is provided a method for preventing and suppressing oral diseases which comprises administering to a patient an effective amount of an oral composition of the present invention. The daily dosage of the oral composition of the present invention will, naturally, vary depending on the age and condition of the patient. However, the oral composition may normally be administered in divided doses of from about 1.5 to 20 enzyme units per day per person in terms of amount of each of dextranase and α-1,3 glucanase.

As explained hereinabove, the oral composition of the present invention is highly effective for not only preventing various oral diseases but also suppressing caries advance.

REFERENCE EXAMPLE 1

Preparation of dextranase

A liquid culture medium (adjusted to pH 8.0), which contained 1.5 w/v percent polypeptone, 0.1 w/v percent yeast extract, 0.2 w/v percent monopotassium phosphate, 0.2 w/v percent monoammonium phosphate and 0.1 w/v percent magnesium sulfate, was inoculated with a strain of the microorganisms belonging to the genus Corynebacterium, Corynebacterium AK-01 (deposited with Technical Research Institute of Microbial Industry, Agency of Industrial Science & Technology, Japan, as an accession number FERM, No. 2505). Cultivation was effected under aeration-agitation at 25° C. for 40 hrs. The cultured broth so obtained was aseptically subjected to centrifugation to remove cells and cell debris. The culture supernate, in turn, was subjected to salting-out with ammonium sulfate, adsorption and desorption over a DEAE column and filtration with Bio-Gel to purify dextranase. There was conducted a test on the presence of other enzymes with respect to the prepared enzyme powder. As a result, it has been found that the prepared enzyme was protease-negative, cellulose-negative and laminaranase-negative. The enzyme thus obtained was freeze-dried to prepare the enzyme powder. The enzyme powder was kept at 4° C. before its use.

On the other hand, there was conducted a test on toxicity of the dextranase prepared above to rats. As a result, it has been found that the $LD_{50}$ (median lethal dose) was more than 500,000 enzyne units per kilogram of rat.

REFERENCE EXAMPLE 2

Preparation of α-1,3 glucanase

Into a 200-liter cultivating tank was charged 120 liters of a liquid culture medium (adjusted to pH 7.0) which contained 1.0 w/v percent polypeptone, 0.1 w/v percent yeast extract, 1.0 w/v percent soluble starch, 0.1 w/v percent magnesium chloride, 0.05 w/v percent calcium chloride and 0.05 w/v percent monopotassium phosphate, and the liquid culture medium was heat-sterilized. The sterilized liquid culture medium was inoculated with 500 ml of a seed cultured broth of a strain of the microorganisms belonging to the genus Pseudomonas, Pseudomonas SK-01 (deposited with Technical Research Institute of Microbial Industry, Agency of Industrial Science & Technology, Japan, as an accession number FERM No. 4273) which seed cultured broth had previously been cultured with shaking in the same kind of liquid medium as that mentioned above. The cultivation under aeration-agitation was then effected at 25° C. for 40 hours. The cultured broth obtained was subjected to centrifugation to remove cells and cell debris. Thus, there was obtained 110 liters of supernatant fluid. To the supernatant fluid was added 70% by volume of ethanol to precipitate α-1,3 glucanase. The precipitated α-1,3 glucanase was subjected to adsorption and desorption over a DEAE column and filtered with Bio-Gel to purify α-1,3 glucanase. The enzyme thus obtained was freeze-dried to prepare the enzyme powder. There was conducted a test on the presence of other enzymes with respect to the prepared enzyme powder. As a result, it has been found that the prepared enzyme was protease-negative, cellulose-negative and laminaranase-negative. The enzyme powder was kept at 4° C. before its use.

On the other hand, there was conducted a test on toxicity of the α-1,3 glucanase prepared above to rats. As a result, it has been found that the $LD_{50}$ (median lethal dose) was more than 75,000 enzyme units per kilogram of rat.

REFERENCE EXPERIMENT 1

Tests of enzymes on substrate-degrading activity

The tests were conducted in order to evaluate substrate-degrading activities of dextranase and α-1,3 glucanase with respect to the case where they are used alone and with respect to the case where they are used in combination.

Water insoluble glucan was prepared as follows. A liquid medium containing 3 w/v percent of trypticase soy broth was inoculated with a strain *Streptococcus Mutans* OMZ-176 and then subjected to stationary cultivation at 37° C. for 20 hours. The resulting cultured broth was subjected to centrifugation to remove cells and cell debris. The culture supernate, in turn, was subjected to salting-out. The resulting precipitate was collected by means of centrifugation and dissolved in distilled water. The obtained solution was dialyzed in a 0.1 M phosphate buffer (pH 6.8) to prepare an insoluble glucan-producing enzyme solution. To the insoluble glucan-producing enzyme solution was added as a substrate sucrose in an amount of 10% w/v and the resulting mixture was allowed to react at 37° C. for 48 hours. The reaction mixture was subjected to centrifugation to obtain insoluble glucan as precipitate. The thus obtained insoluble glucan was suspended in distilled water and the suspension was subjected to centrifugation again. The treatment of the insoluble glucan with trypsin was effected at 37° C. for 15 hours to remove proteins contained in the insoluble glucan. The resulting reaction mixture was subjected to centrifugation to collect the insoluble glucan as precipitate and the precipitate was washed with distilled water and freeze-dried to prepare a dried insoluble glucan.

The insoluble glucan thus obtained was added to a 0.1 M phosphate buffer (pH 6.5) at a ratio of 1.4 mg/ml to form a substrate suspension and the resulting suspension was kept at 37° C.

On the other hand, each of the enzymes prepared in the Reference Examples 1 and 2 was dissolved in a 0.1 M phosphate buffer (pH 6.5) and then diluted. Thus, there were formed, as enzyme solutions, a dextranase solution (0.03 enzyme unit/ml), an α-1,3 glucanase enzyme solution (0.03 enzyme unit/ml) and a mixed solution of both enzymes (each 0.03 enzyme unit/ml). Subsequently, the substrate suspension which had previously been kept at 37° C. was admixed with the respective enzyme solution in equal volumes. The so obtained mixtures were allowed to react at 37° C. for 20, 60, 120 and 180 minutes, respectively. Each of the enzymatic reactions was stopped by heat treatment at 100° C. for 3 minutes. Each of the reaction mixture was subjected to centrifugation. The solubilized sugar in the obtained filtrate was measured according to the anthrone reaction method [J. H. Roe: J. Biol. Chem, 212, 335 (1955)]. As a control, there was employed a 1:1 by volume mixture of the enzyme solution and the substrate suspension which mixture had been subjected to heat treatment in the same manner as mentioned above to stop the enzymatic reaction.

As can be seen from the results illustrated in FIGURE, the combined use of both enzymes has a synergistic effect in solubilization and degradation of the insoluble glucan produced by the above-mentioned cariogenic strain OMZ-176 as compared with the sole use of each enzyme.

REFERENCE EXPERIMENT 2

Substantially the same procedures as in Reference Experiment 1 were repeated except that there were employed, as substrate, insoluble glucans produced by other cariogenic strains, namely *Streptococcus mutans* strain AHT, strain BHT, strain MT-6 and strain HS-6, respectively. There was determined the substrate degrading activity in each case of the sole use and the combined use of the aforesaid enzymes. As a result, a similar synergistic effect in substrate degradation to that of the Reference Experiment 1 was observed when both the enzymes were used together.

To illustrate the synergistic effect of the combined use of both enzymes in more detail, the following animal tests were conducted as Experiments 1 and 2.

EXPERIMENT 1

The following animal tests were conducted with golden hamsters which are said to be a model for smooth surface caries, in order to evaluate the caries-preventing and -suppressing effect of dextranase and α-1,3 glucanase with respect to the case where they are used alone and with respect to the case where they are used in combination.

The animal tests were conducted on sixteen groups of 25-day old golden hamsters, each group consisting of ten animals. Golden hamsters of each group were given for 2 days, as a drinking water, distilled water in which $10^7$/ml of fresh cultured cells of a cariogenic strain resistant to Streptomycin, *Streptococcus mutans* OMZ-176 was suspended. During this period there was given as a diet the caries-inducing powdery diet "Diet 2000" manufactured and sold by Nihon Kurea K.K., Japan. After confirming the deposit of the said strain OMZ-176 within the oral cavities of hamsters of each group, they were given distilled water (10 to 20 gm/animal/day) and the above-mentioned "Diet 2000" (10 to 15 gm/animal/day) containing a sole kind of either dextranase as prepared in Reference Example 1 or α-1,3 glucanase as prepared in Reference Example 2, or a mixture thereof in a varied enzyme ratio as indicated in Table 1.

Time schedules for enzyme administration and the results are summarized in the following Table 1.

TABLE 1

| | Group No. | Amount of enzyme given[1] | | Caries score[4] | Time schedule for enzyme administration |
|---|---|---|---|---|---|
| | | Enzyme I[2] | Enzyme II[3] | | |
| Present invention | 1 | 1 | 1 | 5.2 | Caries preventing test groups: Enzyme given until 61st day (autopsy) immediately after infection with the OMZ-176 strain |
| | 2 | 1 | 0.5 | 9.2 | |
| | 3 | 0.5 | 1 | 10.5 | |
| Comparative | 4 | 2 | 0 | 19.3 | |
| | 5 | 0 | 2 | 22.4 | |
| | 6 | 1 | 0.1 | 19.6 | |
| | 7 | 0.1 | 1 | 21.4 | |
| Present invention | 8 | 1 | 1 | 30.6 | Caries advance suppressing test groups: Enzyme given from 31st day till 61st day after infection with the OMZ-176 strain. |
| | 9 | 1 | 0.5 | 38.9 | |
| | 10 | 0.5 | 1 | 33.4 | |
| Comparative | 11 | 2 | 0 | 78.1 | |
| | 12 | 0 | 2 | 89.2 | |
| | 13 | 1 | 0.1 | 76.4 | |
| | 14 | 0.1 | 1 | 81.0 | |
| Control | 15[5] | 0 | 0 | 29.0 | Autopsy on 31st day after infection with the OMZ-176 strain. |
| | 16[5] | 0 | 0 | 139.5 | Autopsy on 61st day after infection with the OMZ-176 strain. |

Note:
[1]Enzyme units/gm of each of "Diet 2000" diet and distilled water
[2]Dextranase
[3]α-1,3 glucanase
[4]Measured by the Keyes method [Keyes, P.H.: J. Dent. Res., 23, 439-444 (1944)]: The value of the case where 100% of the hamster teeth have been suffered from caries is evaluated as 282.
[5]"Diet 2000" and distilled water each without any enzyme incorporated therein were given with respect to both the controls

EXPERIMENT 2

Substantially the same procedures as in Experiment 1 were repeated with respect to fourteen groups of 25-day old golden hamsters except that the amounts of enzymes were varied as indicated in Table 2.

Time schedules for enzyme administration and the results are summarized in the following Table 2.

TABLE 2

| | Group No. | Amount of enzyme given[1] | | Caries score[4] | Time schedule for enzyme administration |
|---|---|---|---|---|---|
| | | Enzyme I[2] | Enzyme II[3] | | |
| Present invention | 17 | 1 | 1 | 5.4 | Caries preventing test groups: Enzyme given until 61st day |

TABLE 2-continued

| | Group No. | Amount of enzyme given[1] Enzyme I[2] | Enzyme II[3] | Caries score[4] | Time schedule for enzyme administration |
|---|---|---|---|---|---|
| Comparative | 18 | 1 | 0 | 24.2 | (autopsy) immediately after infection with the OMZ-176 strain |
| | 19 | 0 | 1 | 27.8 | |
| | 20 | 2 | 0 | 19.3 | |
| | 21 | 0 | 2 | 23.2 | |
| Present invention | 22 | 1 | 1 | 37.2 | Caries advance suppressing test groups: Enzyme given from 31st day till 61st day after infection with the OMZ-176 strain. |
| Comparative | 23 | 1 | 0 | 84.7 | |
| | 24 | 0 | 1 | 97.0 | |
| | 25 | 2 | 0 | 79.8 | |
| | 26 | 0 | 2 | 91.2 | |
| | 27 | 5 | 0 | 63.6 | |
| | 28 | 0 | 5 | 76.2 | |
| Control | 29[5] | 0 | 0 | 34.2 | Autopsy on 31st day after infection with the OMZ-176 strain. |
| | 30[6] | 0 | 0 | 143.9 | Autopsy on 61st day after infection with the OMZ-176 strain. |

Note:
[1] to [5] above have the same meanings as defined in Table 1.

As is apparent from the caries scores in Tables 1 and 2, carieses of hamsters were synergistically prevented and suppressed when dextranase and α-1,3 glucanase were administered in combination at an enzyme unit ratio of 1:2 to 2:1. By contrast, caries could not be prevented and suppressed effectively when dextranase or α-1,3 glucanase was solely administered and when dextranase and α-1,3 glucanase were administered in combination but the enzyme unit ratio as defined above falls outside of the range.

EXPERIMENT 3

The following animal tests were conducted in substantially the same manner as in Experiment 1 except that in place of hamsters, there were used rats which are said to be a model for fissure carries, so that caries-preventing and-suppressing effects of detranase and α-1,3 glucanase were evaluated with respect to the case where they are used alone and with respect to the case where they are used in combination.

The animal tests were conducted on sixteen groups of 20-day old SD rats, each group consisting of ten animals.

Time schedules for enzyme administration and the results obtained are summarized in the following Tables 3.

TABLE 3

| | Group No. | Amount of enzyme given[1] Enzyme I[2] | Enzyme II[3] | Caries score[4] | Time schedule for enzyme administration |
|---|---|---|---|---|---|
| Present invention | 31 | 1 | 1 | 6.4 | Caries preventing test groups: Enzyme given until 61st day (autopsy) immediately after infection with the OMZ-176 strain |
| | 32 | 1 | 0.5 | 7.4 | |
| | 33 | 0.5 | 1 | 9.5 | |
| Comparative | 34 | 2 | 0 | 13.0 | |
| | 35 | 0 | 2 | 17.5 | |
| | 36 | 1 | 0.1 | 11.6 | |
| | 37 | 0.1 | 1 | 14.0 | |
| Present invention | 38 | 1 | 1 | 29.0 | Caries advance suppressing test groups: Enzyme given from 31st day till 61st day after infection with the OMZ-176 |
| | 39 | 1 | 0.5 | 34.1 | |
| | 40 | 0.5 | 1 | 32.5 | |
| Comparative | 41 | 2 | 0 | 74.0 | |
| | 42 | 0 | 2 | 81.2 | |
| | 43 | 1 | 0.1 | 70.4 | |

TABLE 3-continued

| | Group No. | Amount of enzyme given[1] Enzyme I[2] | Enzyme II[3] | Caries score[4] | Time schedule for enzyme administration |
|---|---|---|---|---|---|
| | 44 | 0.1 | 1 | 64.4 | strain. |
| Control | 45[5] | 0 | 0 | 22.3 | Autopsy on 31st day after infection with the OMZ-173 strain. |
| | 46[5] | 0 | 0 | 95.1 | Autopsy on 61st day after infection with the OMZ-176 strain. |

Note:
[1] to [3] and [5] above have the same meanings as defined in Table 1.
[4] Measured by the Keyes method: The value of the case where 100% of the hamster teeth have been suffered from caries is evaluated as 282.

EXPERIMENT 4

Substantially the same procedures as in Experiment, were repeated with respect to fourteen groups of 20-day old SD rats except that the amounts of enzymes were varied as indicated in Table 4.

Time schedules for enzyme administration and the results are summarized in the following Table 4.

TABLE 4

| | Group No. | Amount of enzyme given[1] Enzyme I[2] | Enzyme II[3] | Caries score[4] | Time schedule for enzyme administration |
|---|---|---|---|---|---|
| Present invention | 47 | 1 | 1 | 6.2 | Caries preventing test groups: Enzyme given until 61st day (autopsy) immediately after infection with the OMZ-176 strain |
| Comparative | 48 | 1 | 0 | 11.3 | |
| | 49 | 0 | 1 | 15.7 | |
| | 50 | 2 | 0 | 10.8 | |
| | 51 | 0 | 2 | 13.1 | |
| Present invention | 52 | 1 | 1 | 24.4 | Caries advance suppressing test groups: Enzyme given from 31st day till 61st day after infection with the OMZ-176 strain. |
| Comparative | 53 | 1 | 0 | 75.3 | |
| | 54 | 0 | 1 | 85.3 | |
| | 55 | 2 | 0 | 68.5 | |
| | 56 | 0 | 2 | 80.2 | |
| | 57 | 5 | 0 | 59.0 | |
| | 58 | 0 | 5 | 63.2 | |
| Control | 59[5] | 0 | 0 | 19.5 | Autopsy on 31st day after infection with the OMZ-176 strain. |
| | 60[6] | 0 | 0 | 91.2 | Autopsy on 31st day after infection with the OMZ-176 strain. |

Note:
[1] to [5] above have the same meanings as defined in Table 3.

As is apparent from the caries scores in Tables 3 and 4, caries of rats were synergistically prevented and suppressed when dextranase and α-1,3 glucanase were administered in combination at an enzyme unit ratio of 1:2 to 2:1. By contrast, caries could not be prevented and suppressed effectively when dextranase or α-1,3 glucanase was solely administered and when dextranase and α-1,3 glucanase were administered in combination but enzyme unit ratio falls outside the range as defined above.

The following Examples are given to illustrate the present invention in more detail but should not be construed as limiting the scope of the invention.

EXAMPLE 1

A toothpaste was prepared with the following formulation wherein all figures are W/W percents.

| | |
|---|---|
| Dicalcium phosphate dihydrate | 45 |
| Glycerine | 25 |
| Sodium carboxymethylcellulose | 0.5 |
| Carrageenan | 0.5 |
| Polysorbate 80 | 1.0 |
| Saccharin (sodium salt) | 0.15 |
| Dextranase (enzyme activity: 100,000 enzyme units/gm) | 0.002 |
| α-1,3 glucanase (enzyme activity: 15,000 enzyme units/gm) | 0.02 |
| Flavor | 1.0 |
| Water | 26.828 |

EXAMPLE 2

A liquid mouth rinse was prepared with the following formulation wherein all figures are W/W percents.

| | |
|---|---|
| Calcium chloride | 0.2 |
| Glycerine | 5.0 |
| Ethanol | 4.0 |
| l-Menthol | 0.1 |
| Cinnamon oil | 0.1 |
| Saccharin (sodium salt) | 0.1 |
| Dextranase (enzyme activity: 100,000 enzyme units/gm) | 0.002 |
| α-1,3 glucanase (enzyme activity: 15,000 enzyme units/gm) | 0.02 |
| Water | 90.478 |

EXAMPLE 3

A troche was prepared with the following formulation wherein all figures are W/W percents

| | |
|---|---|
| Gum arrabic | 6.0 |
| Glucose | 70 |
| Galactose | 1.0 |
| Dextranase (enzyme activity: 100,000 enzyme units/gm) | 0.003 |
| α-1,3 glucanase (enzyme activity: 15,000 enzyme units/gm) | 0.03 |
| Water | 22.967 |

EXAMPLE 4

A chewing gum was prepared with the following formulation wherein all figures are W/W percents.

| | |
|---|---|
| Gum base | 20 |
| Calcium carbonate | 1.0 |
| Starch syrup | 20 |
| Glucose | 57 |
| Galactose | 1.0 |
| Dextranase (enzyme activity: 100,000 enzyme units/gm) | 0.003 |
| α-1,3 glucanase (enzyme activity: 15,000 enzyme units/gm) | 0.03 |
| Flavor | 0.967 |

-continued

What is claimed is:

1. An oral composition synergistic at pH 6.5 which comprises a pharmaceutically acceptable carrier, dextranase and α-1,3 glucanase, said dextranase and said α-1,3 glucanase both being present in an amount of 0.5 to 100 enzyme units per gram of said oral composition, said dextranase being present in an enzyme unit ratio of 1:2 to 2:1 relative to said α-1,3 glucanase, said dextranase being one prepared from dextranase-biosynthesizing microorganisms belonging to the genus Corynebacterium, said α-1,3 glucanase being one prepared from an α-1,3 glucanase-biosynthesizing microorganism belonging to the genus Pseudomonas.

2. A method for preventing and suppressing smooth surface dental caries, fissure dental caries and gingivities induced by the formation of dental plaque formed through adhesion to the teeth and gingival of viscous glucans produced from sucrose by the action of caries causing streptococci, *Streptococous mutans*, given to the oral cavities of golden hamsters, which are said to be a model for smooth surface caries, and rats, which are said to be a model for fissure caries, which comprises administering to a patient an effective amount of an oral composition synergistic at pH 6.5 comprising a pharmaceutically acceptable carrier, dextranase and α-1,3 glucanase, said dextranase and said α-1,3 glucanase both being present in an amount of 0.5 to 100 enzyme units per gram of said oral composition, said dextranase being present in an enzyme-unit ratio of 1:2 to 2:1 relative to said α-1,3 glucanase, said dextranase being one prepared from dextranase-biosynthesizing microorganisms belonging to the genus Corynebacterium, said α-1,3 glucanase being one prepared from an α-1,3 glucanase biosynthesizing microorganism belonging to the genus Pseudomonas.

3. A method for preventing and suppressing oral diseases according to claim 2, wherein said effective amount of the oral composition is about 1.5 to 20 enzyme units per day for person in terms of amount of each of dextranase and α-1,3 glucanase.

4. A method according to claim 1, wherein said dextranase-biosynthesizing microorganism is a strain Corynebacterium AK-01.

5. A method according to claim 1, wherein said α-1,3 glucanase-biosynthesizing microorganism is a strain Pseudomonas SK-01.

6. A method according to claim 2, wherein said dextranase-biosynthesizing microorganism is a strain Corynebacterium AK-01.

7. A method according to claim 2, wherein said α-1,3 glucanase-biosynthesizing microorganism is a strain Pseudomonas SK-01.

* * * * *